United States Patent [19]

Peabody

[11] Patent Number: 5,309,924
[45] Date of Patent: May 10, 1994

[54] SPILL-PROOF BLOOD COLLECTION DEVICE

[76] Inventor: Alan M. Peabody, 204 Pebble Creek Way, Taylors, S.C. 39687

[21] Appl. No.: 875,312

[22] Filed: Apr. 29, 1992

[51] Int. Cl.$^5$ ............................................. A61M 1/00
[52] U.S. Cl. ................................. 128/765; 128/760; 604/403
[58] Field of Search ............... 128/760, 762, 763, 764, 128/765, 766, 767; 604/403, 408

[56] References Cited

U.S. PATENT DOCUMENTS

| | | | |
|---|---|---|---|
| 3,340,869 | 12/1967 | Bane | 128/765 |
| 3,460,529 | 8/1969 | Leucci | 128/766 X |
| 3,473,524 | 10/1969 | Drewe | 128/765 |
| 3,557,778 | 1/1971 | Hughes | 128/766 |
| 3,796,542 | 3/1974 | Kline | 128/763 X |
| 3,933,439 | 1/1976 | McDonald | 128/765 X |
| 4,036,232 | 7/1977 | Genese | 128/763 X |

*Primary Examiner*—Robert A. Hafer
*Assistant Examiner*—Sam Rimell
*Attorney, Agent, or Firm*—Cort Flint

[57] ABSTRACT

A blood collection device is disclosed which includes a blood collection tube assembly and a collection container assembly. The collection tube assembly comprises a link of flexible tubing having a venipuncture needle carried on a first end and an outlet carried on a second end. A flow control valve is carried near the outlet end and blocks a central passage of the collection tube in a closed position. The collection container assembly includes an expandable plastic tube which may be expanded by an exterior spring to cause a slight vacuum in the container and assist the blood withdrawal tube. A transfer tube communicates with the interior of the collection container and includes a blunt needle on an inlet end. The blunt needle engages the flow control valve to open the valve and open and allow blood to flow outwardly after the venipuncture needle has been inserted into a vein. The collection tube may be left in the vein while the collection chamber is removed and replaced without the fear of blood spillage since the flow control valve will return to the closed position once the blunt needle is withdrawn.

14 Claims, 2 Drawing Sheets

SPILL-PROOF BLOOD COLLECTION DEVICE

BACKGROUND OF THE INVENTION

The invention relates to a device for collecting blood from a human body in a spill-proof manner so as to prevent the spread of infectious diseases.

In the present era of blood-borne infectious diseases such as Hepatitis and AIDS, the health care industry has become rightfully concerned with unwanted spillage of a patient's blood. This concern has lead to the institution of universal precautions to guard workers against accidental contamination by a patient's blood. These diseases can be spread by a very small inoculum of blood, such as the amount in the hollow portion of a hypodermic needle. The currently available systems for collecting blood specimens for laboratory analysis are subject to some blood spillage. The health care workers are exposed to this blood during the time the specimen is being drawn, during the clean-up, and probably for some time afterwards if the clean-up is not thorough. The problems with the typical needle and syringe method of blood collection are obvious, particularly, if more than one syringe of blood is needed. The most popular method, the Vacutainer TM, tends to allow blood to drip from the end of the collection needle while the tubes are being changed. A covered needle has been proposed, but it has not been particularly effective. Both the needle holder and the specimen tubes usually become contaminated with the patient's blood. In addition, the tubes are made of glass and easily break during centrifugation and shipping.

U.S. Pat. No. 3,933,439 issued to McDonald discloses a blood collection device for taking a sample of blood from a patient and dispensing a predetermined volumetric sample for analysis. A blood collection needle is in fluid communication with the interior of an expandable container which assists in drawing the blood. The device does not address the problem of blood spillage. There is no practical way to shut off the flow of blood from the needle when it is in a vein except by plugging the end of the needle with a collection chamber. Changing the collection chamber on the device could cause an unacceptable amount of blood spillage. It would not be practical to make the blood collection chamber large enough to draw all of the required blood at one time. It is not uncommon to draw 50 to 75 ml or more of blood for a series of tests. Blood flow is frequently too slow to allow one to collect both the clotted and anticoagulated specimens without changing the collection chamber.

Accordingly, an object of the invention is to provide a blood collection device which prevents blood spillage during use.

Another object of the invention is to provide a blood collection device wherein multiple specimens of blood may be taken in multiple containers using a single venipuncture needle without blood spillage.

SUMMARY OF THE INVENTION

The above objectives are accomplished according to the invention by providing a spill proof blood collection device which includes a disposable, plastic, blood collection tube having a venipuncture needle carried by a first end of the tube and an outlet formed on its second end. A check valve is carried in the tube near the second end having a sealed valve element which prevents the spillage of blood from the tube's outlet end when it is sealed. A specimen collection container is provided having a transfer tube which extends from the collection container and has a blunt, hollow needle. The blunt needle is inserted into the outlet end of the blood collection tube to open the valve element of the check valve and form a spill proof passage for blood to flow from the venipuncture needle. The blood then flows through the blood collection tube, through the transfer tube, and into the collection container. A clamping mechanism is carried by the blood collection tube for temporarily restricting blood flow through the tube to further minimize the possibility of blood flow spillage from the outlet end. The collection container preferably includes a closed, longitudinally collapsible, elastic container. The collection container is movable between a normally extended position which has a larger interior volume and a compressed position which has a smaller interior volume.

A manual release is provided for temporarily securing the container in its compressed position. The transfer tube is composed of a heat sealable material which can be cut and heat sealed to allow for the discarding of the blunt needle when the collection container is filled and ready for storage. The collection container comprises a substantially rigid top portion and a lower portion consisting of collapsible, corrugated bellows. The elasticity and compressibility of the collection container is enhanced by longitudinally mounting a spring on an exterior of the container.

DESCRIPTION OF THE DRAWINGS

The construction designed to carry out the invention will hereinafter be described, together with other features thereof.

The invention will be more readily understood from a reading of the following specification and by reference to the accompanying drawings forming a part thereof, wherein an example of the invention is shown and wherein.

DESCRIPTION OF A PREFERRED EMBODIMENT

Figure 1:
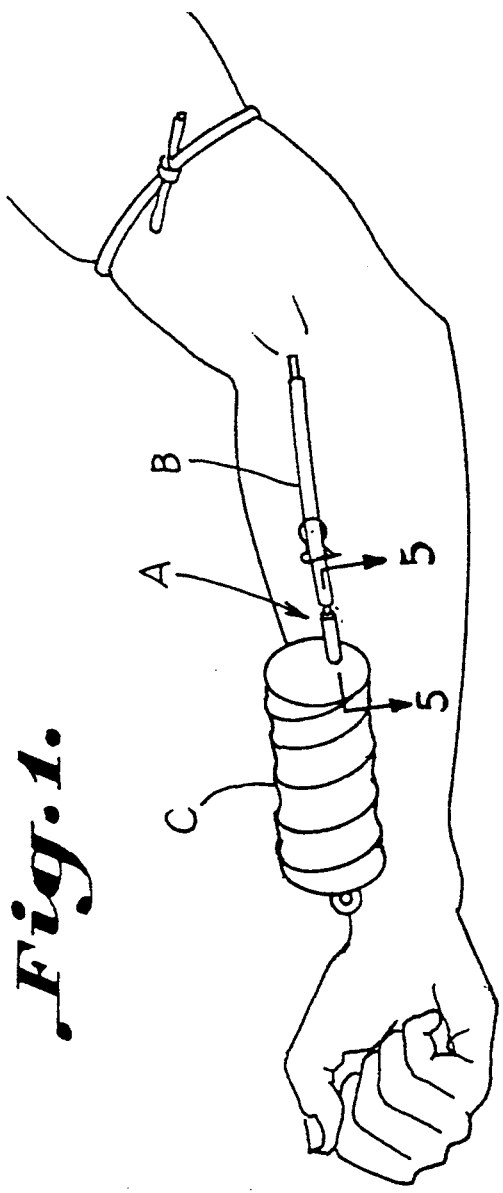
FIG. 1 is a perspective view illustrating the collection of a blood specimen utilizing a spill-proof blood collection device according to the invention.
Figure 2:
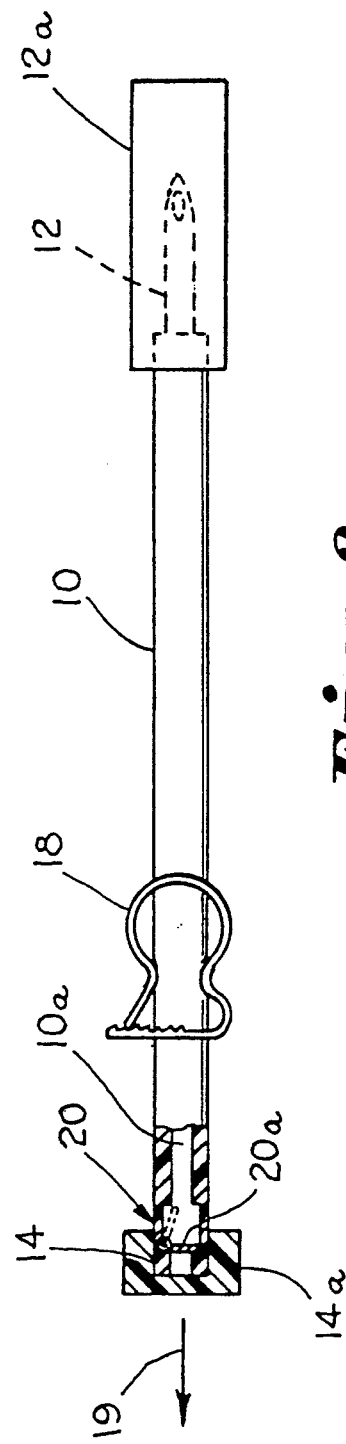
FIG. 2 is an elevation of a collection tube assembly for a spill-proof blood collection device according to the invention.
Figure 3:
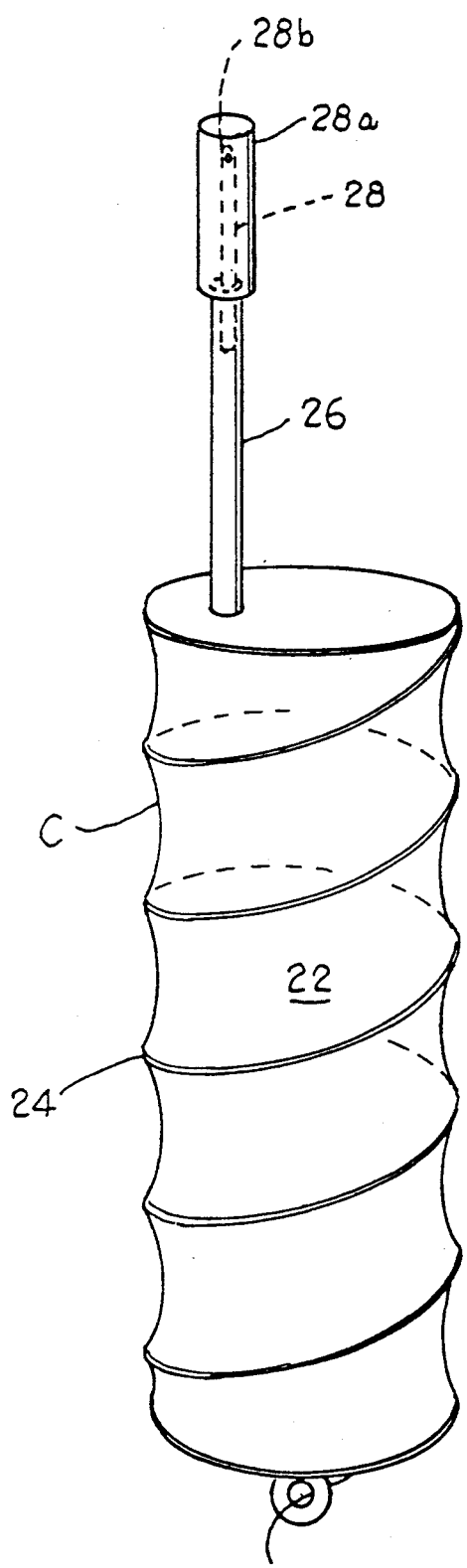
FIG. 3 is a perspective view of a collection container assembly for a blood collection device constructed according to the present invention with the collection chamber in an expanded configuration.
Figure 4:
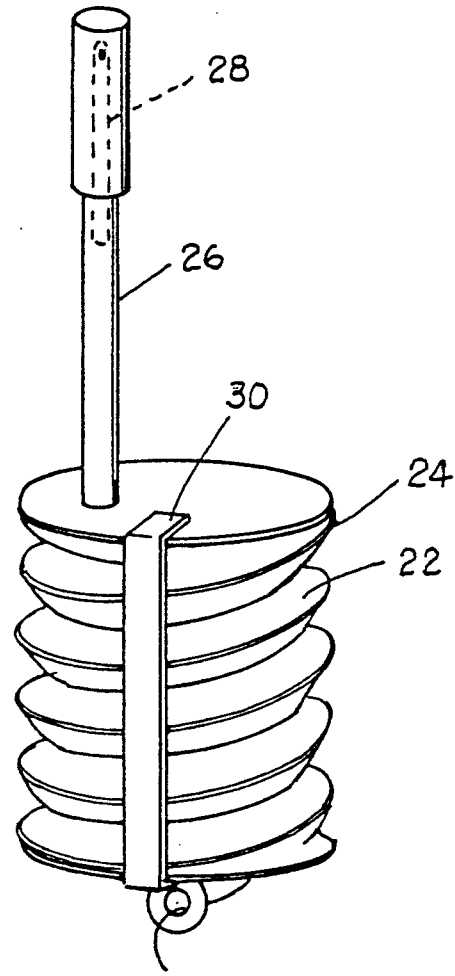
FIG. 4 is a perspective view of a collection container according to the invention in a pressed configuration.
Figure 5:
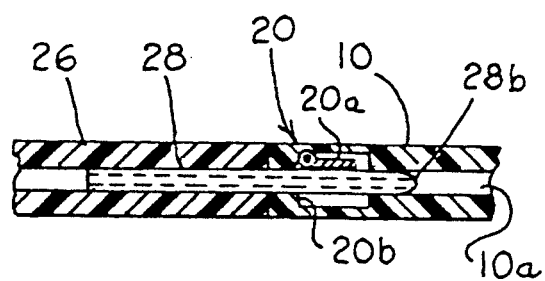
FIG. 5 is a sectional view taken along line 5—5 of FIG. 1.

Referring now in more detail to the drawings, a blood collection device, designated generally as A, is illustrated which includes a collection tube assembly B, and a collection container C. Collection tube assembly B includes a collection tube 10 having a venipuncture needle 12 carried by one end covered by a sterility cap 12a when not in use. Collection tube 10 includes an open end 14 covered by a sterility cap 14a when not in use, and an internal passage 10a. Preferably, collection tube 10 includes a length of flexible plastic tubing and the assembly includes a finger clamp 18 for shutting off flow in tubing passage 10a. In addition, there is a means for positively controlling the control of the flow of blood in passage 10a, and preventing the flow of blood from the vein through the tubing in an outward direction, as shown by arrow 19. Preferably, the positive flow control means includes a valve means 20 which prevents the flow of blood in the outward direction through passage 10a and open end 14 when venipuncture needle 12 is inserted in a vein. As can best be seen in FIGS. 3 and 4, collection container C includes an expandable container 22 which may be compressed and subsequently expanded by means of a spring 24. Container 22 is preferably made from a compressible plastic tube constructed from material that is non-reactive to blood such as that used for blood banking. Extending into collapsible container 22 is a transfer tube 26 having a blunt needle 28 carried on a distal end which is covered by a sterility cap 28a when not in use. A retaining clip 30 keeps the collapsible container 22 compressed when not in use.

In use, venipuncture needle 10 is inserted in a vein of a patient. The flow of blood is prevented by positive flow control means 20. In addition, the finger clamp 18 on tubing 10 may be closed. In the event that the health care worker forgets to close the finger clamp, valve means 20 will positively prevent the flow of blood outwardly. Next, blunt needle 28 of transfer tube 26 is inserted in open end 14 of collection tube 10. In the illustrated embodiment, valve means 20 is in a form of a flap check valve having a flap element 20a which sealed on a seat 20b and moved away therefrom by engagement with an end 28b of blunt needle 28. The end of blunt needle 28 engages valve means 20 and opens the valve means to place the interior of expandable container 22 in fluid communication with the blood in the patient's vein. Retaining clamp 18 is then released from the expandable container and the blood is drawn from the patient in a spill-proof manner. Once the desired amount of blood has been withdrawn, the finger clamp is closed and the blunt needle of the collection container is withdrawn from the collection tube. This also closes valve means 20 to ensure positively that blood does not flow or spill outwardly from the collection tube. Even in the event the finger clamp is not closed, there will be no blood spillage. Blunt needle 28 is then cut from transfer tube 26. Transfer tube 26 is then heat sealed. Another collection container may be connected to collection tube 10 in the same manner by inserting blunt needle 28 into open end 14 of collection tube to open the valve and start the flow and collection of blood. As many containers as needed may be used in this manner to collect a desired quantity of blood and number of specimens.

Thus, it can be seen that an advantageous construction and method can be had according to the invention for a device for collecting blood in a spill-proof manner. A flow of blood from a patient's vein is not allowed through a venipuncture needle and collection tube until a collection container has been inserted in the collection tube in a positive manner so as to open a valve that normally prevents flow of blood outwardly through the collection tube. In this manner, spill-proof collection of blood is assured.

While a preferred embodiment of the invention has been described using specific terms, such description is for illustrative purposes only, and it is to be understood that changes and variations may be made without departing from the spirit or scope of the following claims.

What is claimed is:

1. A blood collection device for collecting blood without spillage comprising:
   a blood collection tube having a venipuncture needle carried on one end;
   an open end formed on an opposing end of said collection tube in fluid communication with said needle;
   a removable specimen collection container including means for attachment in fluid communication to said blood collection tube and for removal from said collection tube after collection of a prescribed blood amount;
   a transfer tube carried by said specimen container in fluid communication with an interior of said container;
   positive blood flow control means carried within said blood collection tube which prevents the outward flow of blood from said collection tube from said person's vein; and
   a hollow needle carried by a free end of said transfer tube which engages said flow control means when said needle is inserted into said collection tube to facilitate said attachment of said collection container and open said flow control means and allow the flow of blood outwardly through said collection tube when said needle is inserted in said collection tube so that a plurality of said collection containers may be attached to and removed from said blood collection tube without blood spillage.

2. The device of claim 1 including sterilization means carried by said first and second ends of said collection tube for maintaining said venipuncture needle and said opening in a sterilized condition.

3. The device of claim 1 wherein said flow control means comprises a check valve having a closure member which is opened by engagement and actuation by said needle of said transfer tube.

4. The device of claim 1 wherein said collection tube is flexible and includes a clamp for pinching said flexible tubing to close off the flow of blood through said flexible tube.

5. The device of claim 1 wherein said specimen container includes an expandable container.

6. The device of claim 5 wherein said expandable container includes a flexible plastic tube; a expansion spring having one end affixed to a first end of said first plastic tube and a second end affixed to a second end of said plastic tube; means for maintaining said plastic tube and spring in a compressed configuration and for allowing said plastic tube to expand when said means is released to an expanded position whereby a slide vacuum is created to assist in blood withdrawal.

7. The device of claim 1 wherein said transfer tube includes a heat sealable plastic tube which may be heat sealed after said specimen of blood is collected.

8. A spill proof blood collection device comprising:
   a disposable, plastic, blood collection tube having a venipuncture needle carried by a first end and an outlet formed on its second end;
   a removable blood collection container having means for attachment in fluid communication to said blood collection tube and for removal from said collection tubes after collection of a prescribed blood amount;
   a valve carried in the blood collection tube near said second end having a sealed valve element which prevents the spillage of blood from the tube's outlet end when it is sealed; and a transfer tube extending from said collection container and having a hollow needle which is inserted into said outlet end of the blood collection tube to facilitate said attachment of said collection container and open said valve element of said check valve and form a spill proof passage for blood to flow from said venipuncture needle, through said blood collection tube, said transfer tube, and into said collection container so that a plurality of said collection containers may be attached to and removed from said blood collection tube without blood spillage.

9. The device of claim 8 including a clamping mechanism carried by said blood collection tube for temporarily restricting blood flow through the tube to further minimize the possibility of blood flow spillage from said outlet end.

10. The device of claim 8 wherein said collection container includes a closed, longitudinally collapsible, elastic container movable between a normally extended position having a larger interior volume and a compressed position having a smaller interior volume.

11. The device of claim 10 including manually releasable means for temporarily securing the container in its compressed position.

12. The device of claim 10 wherein said transfer tube is composed of a heat sealable material which can be cut and heat sealed to allow for the discarding of said needle when said collection container is filled and ready for storage.

13. The device of claim 10 wherein said collection container comprises a substantially rigid top portion and a lower portion consisting of collapsible, corrugated bellows.

14. The device of claim 10 wherein the elasticity and compressibility of said collection container is enhanced by longitudinally mounting a spring on an exterior of said container.

* * * * *